US009258996B2

(12) United States Patent
Klingelhoefer et al.

(10) Patent No.: US 9,258,996 B2
(45) Date of Patent: Feb. 16, 2016

(54) COMPOSITION COMPRISING A PESTICIDE AND AN ALKOXYLATE OF ISO-NONYLAMINE

(75) Inventors: Paul Klingelhoefer, Mannheim (DE); Sophie Vogel, Mannheim (DE); Kevin Huyghe, Mannheim (DE); Gerd Haderlein, Grünstadt (DE); Gerhard Schnabel, Elsenfeld (DE); Marc Nolte, Mannheim (DE); Richard Roger Evans, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 248 days.

(21) Appl. No.: 13/048,946

(22) Filed: Mar. 16, 2011

(65) Prior Publication Data
US 2011/0230342 A1 Sep. 22, 2011

Related U.S. Application Data

(60) Provisional application No. 61/314,600, filed on Mar. 17, 2010.

(51) Int. Cl.
A01N 25/30 (2006.01)
A01N 25/22 (2006.01)
A01N 57/20 (2006.01)

(52) U.S. Cl.
CPC ................ A01N 25/30 (2013.01); A01N 25/22 (2013.01)

(58) Field of Classification Search
CPC ............................ A01N 25/30; A01N 25/22
USPC .................................................. 504/100, 206
See application file for complete search history.

(56) References Cited

U.S. PATENT DOCUMENTS

| 4,460,789 | A | * | 7/1984 | Casciani ................... 564/504 |
| 5,530,127 | A | | 6/1996 | Reif et al. |
| 5,668,085 | A | | 9/1997 | Forbes et al. |
| 5,750,468 | A | | 5/1998 | Wright et al. |
| 2002/0016264 | A1 | * | 2/2002 | Shannon et al. ............. 504/364 |
| 2002/0137634 | A1 | | 9/2002 | Krause et al. |
| 2006/0019828 | A1 | | 1/2006 | Becher et al. |
| 2007/0249560 | A1 | | 10/2007 | Leatherman et al. |
| 2008/0261814 | A1 | | 10/2008 | Zhu et al. |
| 2009/0114879 | A1 | | 5/2009 | Hellsten et al. |
| 2009/0286684 | A1 | | 11/2009 | Scherl et al. |
| 2010/0317521 | A1 | | 12/2010 | Correia |
| 2011/0039703 | A1 | | 2/2011 | Correia |
| 2011/0177945 | A1 | | 7/2011 | Klingelhoefer et al. |
| 2011/0201497 | A1 | | 8/2011 | Klingelhoefer et al. |

FOREIGN PATENT DOCUMENTS

| CA | 2 786 239 | 7/2011 |
| DE | 10 2005 037 971 | 2/2007 |
| EP | 0 696 572 | 2/1996 |
| HU | 45468 | 7/1988 |
| WO | WO 01/97614 | 12/2001 |
| WO | WO 02/102153 | 12/2002 |
| WO | WO 2006/034459 | 3/2006 |
| WO | WO 2007/030312 | 3/2007 |
| WO | WO 2008/111928 | 9/2008 |
| WO | WO 2009/004044 | 1/2009 |
| WO | WO 2009/120621 | 10/2009 |
| WO | WO 2010/068746 | 6/2010 |
| WO | WO 2011/086115 | 7/2011 |
| WO | WO 2011/104211 | 9/2011 |
| WO | WO 2012/116939 | 9/2012 |
| WO | WO 2013/189777 | 12/2013 |

OTHER PUBLICATIONS

Tsui, Martin, "Aquatic toxicity of glyphosate-based formulations: comparison between different organisms and the effects of environmental factors", Chemosphere, 2003, pp. 1189-1197, vol. 52, Elsevier Science Ltd.
Office Action dated Sep. 28, 2012, from U.S. Appl. No. 13/007,187.
Office Action dated Jan. 12, 2015 in U.S. Appl. No. 14/089,045.
Office Action dated Jan. 13, 2015 in U.S. Appl. No. 14/281,304.

* cited by examiner

Primary Examiner — John Pak
Assistant Examiner — Andriae M Holt
(74) Attorney, Agent, or Firm — Brinks Gilson & Lione

(57) ABSTRACT

The present invention relates to a composition comprising a pesticide and an alkoxylate. Moreover, the invention relates to the alkoxylate, to a process for its preparation and to its use as adjuvant in pesticide-comprising spray mixtures. The invention furthermore relates to a method of controlling phytopathogenic fungi and/or undesired vegetation and/or undesired insect or mite attack and/or for regulating the growth of plants, wherein the composition is allowed to act on the respective pests, their environment or the plants to be protected from the respective pest, on the soil and/or on undesirable plants and/or the crop plants and/or their environment. Furthermore, the invention relates to seed comprising the composition.

10 Claims, No Drawings

COMPOSITION COMPRISING A PESTICIDE AND AN ALKOXYLATE OF ISO-NONYLAMINE

This application claims the benefit of U.S. Provisional Application No. 61/314,600, filed Mar. 17, 2010, the entire contents of which are hereby incorporated herein by reference.

The present invention relates to a composition comprising a pesticide and an alkoxylate. Moreover, the invention relates to the alkoxylate, to a process for its preparation and to its use as adjuvant in pesticide-comprising spray mixtures. The invention furthermore relates to a method of controlling phytopathogenic fungi and/or undesired vegetation and/or undesired insect or mite attack and/or for regulating the growth of plants, wherein the composition is allowed to act on the respective pests, their environment or the plants to be protected from the respective pest, on the soil and/or on undesirable plants and/or the crop plants and/or their environment. Furthermore, the invention relates to seed comprising the composition. The present invention comprises combinations of preferred features with other preferred features.

Alkoxylates and their use in agrochemical formulations as adjuvants are generally known:

WO 2009/004044 discloses a herbicidal composition comprising a phenoxy-acid herbicide and an alkoxylated alkylamine as adjuvant.

U.S. Pat. No. 5,668,085 discloses a herbicidal composition comprising an aqueous solution of glyphosate and surfactant. The surfactant may be an alkoxylated alkylamine, the alkyl group comprising 8 to 22 carbon atoms.

WO 2007/97614 discloses herbicidal agents comprising a herbicide and a surfactant, which, for example, may be an alkoxylated alkylamine.

DE 10 2005 037 971 discloses compositions comprising fatty alcohol alkoxylates and tertiary amines comprising alkoxy groups. This mixture can be employed as activity enhancer in agrochemical formulations.

Alkoxylated alkylamines, in particular commercially available ethoxylated tallow fatty amines (POEA), have important toxic properties (such as irritation of the skin and the eyes) and ecotoxic properties (such as high ecotoxicity to aquatic organisms such as algae and daphnias). Thus, for example, POEA (CAS No. 61791-26-2), which is frequently present in Roundup® herbicides as a wetter, is considered to be relatively toxic to aquatic organisms (Tsui and Chu, Chemosphere 2003, 52, 1189-1197).

It was therefore an object of the present invention to find an adjuvant which is well suited to herbicides such as glyphosate while being less toxic (especially lower toxicity to aquatic organisms). Furthermore, the adjuvant should make possible a storage-stable formulation of the pesticides.

The object was solved by a composition comprising a pesticide and an alkoxylate, wherein the alkoxylate is an amine alkoxylate (A)

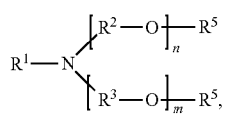

(A)

or a quaternized derivative (AQ)

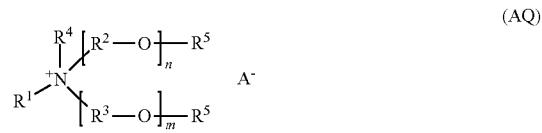

(AQ)

of the amine alkoxylate (A), where
$R^1$ is a branched aliphatic alkyl radical $C_9H_{19}$,
$R^2$, $R^3$, and $R^7$ independently of one another are ethylene, propylene, butylene or a mixture of these,
$R^4$ is an H, —OH, —OR$^6$, —[R$^7$—O]$_p$—R$^5$, $C_1$-$C_6$-alkyl or an oxygen anion,
$R^5$ is an H, $C_1$-$C_6$-alkyl, $C_2$-$C_6$-alkenyl, $C_2$-$C_6$-alkynyl, —SO$_3$R$^a$, —P(O)OR$^b$OR$^b$, —CH$_2$CO$_2$R$^d$ or —C(O)R$^e$,
$R^6$ is a $C_1$-$C_6$-alkyl, $C_2$-$C_6$-alkenyl or $C_2$-$C_6$-alkinyl,
$R^a$ and $R^d$ independently of one another are an H, inorganic or organic cations,
$R^b$ and $R^c$ independently of one another are an H, inorganic or organic cations, $C_1$-$C_6$-alkyl, $C_2$-$C_6$-alkenyl or $C_2$-$C_6$-alkynyl,
$R^e$ is $C_1$-$C_{22}$-alkyl, $C_2$-$C_{22}$-alkenyl, $C_2$-$C_{22}$-alkinyl, $C_6$-$C_{22}$-aryl, $C_7$-$C_{22}$-alkylaryl,
n, m and p independently of one another are a value from 1 to 30, and
A– is an agriculturally acceptable anion, or, if $R^3$ is an oxygen anion, A– is absent.

Preferably, the composition according to the invention comprises a pesticide and an alkoxylate, wherein the alkoxylate is an amine alkoxylate (A).

The radical $R^1$ is a branched aliphatic alkyl radical $C_9H_{19}$. Examples of $R^1$ are, amongst others, 2-methyl-1-octanol, 2-ethyl-1-heptanol, 2-propyl-1-hexanol, 3-methyl-4-hydroxymethylheptane, 3-methyl-3-hydroxymethylheptane or 2-hydroxymethyl-3-methylheptane. Preferably, $R^1$ comprises a plurality of different branched aliphatic $C_9H_{19}$ alkyl radicals. The mean degree of branching of $R^1$ is in most cases 1.01 to 2.5, preferably 1.05 to 1.8, especially preferably 1.1 to 1.5, very especially preferably 1.2 to 1.3.

In this context, the term "degree of branching" is defined in principle in the known manner as the number of methyl groups in a molecule of the alcohol minus 1. The mean degree of branching is the statistic mean of the degrees of branching of all molecules of a sample. In other words, the radical $R^1$ employed may take the form of a mixture of different alkyl groups $C_9H_{19}$. Accordingly, the alcohol $R^1$—OH, which is employed as starting material for the synthesis, may take the form of a mixture of different alcohols.

The mean degree of branching can be determined as follows by $^1$H NMR spectroscopy: to this end, a sample of the alcohol $R^1$—OH is first subjected to derivatization with trichloroacetyl isocyanate (TAI). In this process, the alcohols are converted into the carbamic esters. The signals of the esterified primary alcohols are located at δ =4.7 to 4.0 ppm, those of the esterified secondary alcohols (if present) at approximately 5 ppm, and water present in the sample reacts with TAI to give carbamic acid. All methyl, methylene and methyne protons are in the range of from 2.4 to 0.4 ppm. The signals <1 ppm are assigned to the methyl groups. The mean degree of branching (iso index) can be calculated from the spectrum thus obtained, as follows:

Iso Index=((F(CH$_3$)/3)/(F(CH$_2$—OH)/2))−1, where F(CH$_3$) represents the signal area corresponding to the methyl protons and F(CH$_2$—OH) represents the signal area of the methylene protons in the CH$_2$—OH group.

Preferably, n has a value of from 1 to 20, especially preferably from 1 to 15. Preferably, m has a value of from 1 to 20, especially preferably from 1 to 15. Preferably, p has a value of from 1 to 30, especially preferably from 1 to 20. The values of n, m and o are normally average values as they mostly arise upon the alkoxylation with alkoxides. Therefore, n, m and o can not only be integers, but also all values between the integers.

Preferably, in the case of the amine alkoxylate (A), the total of n and m is 2 to 40 and in its quaternized derivative (AQ) the total of n, m and p is 3 to 80.

In the case of the amine alkoxylate (A) the total of n and m is especially preferably 3 to 30 and specifically 5 to 25. In a further especially preferred embodiment, the total of n and m is 6 to 9, in particular 6.5 to 8.5 and in particular 6.9 to 7.9. In a further especially preferred embodiment, the total of n and m is 11 to 40, in particular 12 to 30 and in particular 13.5 to 25. In a further especially preferred embodiment, the total of n and m is 8 to 13, in particular 9 to 11.

In the case of the quaternized derivative (AQ) of the amine alkoxylate (A), the total of n, m and p is especially preferably 3 to 40 and specifically 5 to 25. In an especially preferred embodiment, the total of n, m and p is 8 to 13, in particular 9 to 11.

$R^2$, $R^3$ and $R^7$ are preferably independently of one another ethylene, ethylene and propylene, ethylene and butylene, or ethylene, propylene and butylene. In a further preferred embodiment, $R^2$, $R^3$ and $R^7$ are propylene. In a further preferred embodiment, $R^2$, $R^3$ and $R^7$ are butylene. Especially preferably $R^2$, $R^3$ and $R^7$ independently of one another are ethylene, or ethylene and propylene. Very especially preferably, $R^2$, $R^3$ and $R^7$ are ethylene.

If $R^2$, $R^3$ or $R^7$ comprise a butylene radical, the latter may be present as a n-butylene, an isobutylene or a 2,3-butylene group, with n-butylene and isobutylene being preferred and n-butylene being most preferred.

$R^2$, $R^3$ and $R^7$ independently of one another may be a mixture of ethylene, propylene or butylene. In this context, for example one or all radicals $R^2$, $R^3$ and $R^7$ may comprise a mixture of these groups in each alkoxylate chain. Such mixtures can be linked to one another in any desired order, for example randomly or blockwise (such as one block ethylene and one block propylene). Also, it is possible for in each case one or more of the radicals $R^2$, $R^3$ and $R^7$ a complete alkoxylate chain to be composed of different alkylene groups. For example, $R^2$ and $R^3$ may be composed of ethylene and $R^7$ of propylene.

$R^4$ is preferably an H, OH, $C_1$-$C_4$-alkyl or an oxygen anion, it is especially preferably an H, methyl, butyl or an oxygen anion. In a specifically preferred embodiment, $R^4$ is a methyl. In a further specifically preferred embodiment, $R^4$ is an oxygen anion. In a further specifically preferred embodiment, $R^4$ is an H.

$R^5$ is preferably an H or $C_1$-$C_6$-alkyl, especially preferably an H or methyl, in particular H.

$R^6$ is preferably a $C_1$-$C_6$-alkyl, such as methyl.

$R^a$ and $R^d$ independently of one another are H, or inorganic or organic cations which can carry one or more positive charges. Examples of inorganic cations are cations of ammonium, $Na^+$, $K^+$, $Mg^{2+}$, $Ca^{2+}$ or $Zn^{2+}$. Examples of organic cations are methylammonium, dimethylammonium, trimethylammonium, tetramethylammonium, (2-hydroxyethyl)ammonium, bis(2-hydroxyethyl)ammonium, tris(2-hydroxyethyl)ammonium, tetra(2-hydroxyethyl)ammonium. Preferably $R^a$ and $R^d$ independently of one another are H or inorganic cations. If an inorganic or organic cation is present, then the associated anionic group would be formed on $R^6$ by the corresponding functional group (for example —$SO_3$—, —P(O)O—O— or —$CH_2CO_2$—).

$R^b$ and $R^c$ preferably independently of one another are H, inorganic or organic cations. Suitable inorganic or organic cations are those mentioned under $R^a$.

In a further embodiment, in the case of the quaternary derivative (AQ), the radicals $R^a$, $R^b$, $R^c$ and $R^d$ independently of one another can be organic cations, the cationic group being the quaternary nitrogen cation of AQ itself. In this case, AQ could therefore form a zwitter ion, the anionic group being formed on $R^6$ in AQ by the corresponding functional group (for example —$SO_3$—, —P(O)O—O— or —$CH_2CO_2$—), and the cationic group being formed by the quaternary nitrogen of AQ. In this zwitter-ionic form of AQ, the presence of an agriculturally acceptable anion A– is optional.

$R^e$ is preferably $C_1$-$C_{12}$-alkyl, $C_1$-$C_{12}$-aryl or $C_1$-$C_{12}$-alkylaryl, especially preferably $C_1$-$C_6$-alkyl.

A– is an agriculturally acceptable anion, as they are generally known to the skilled worker. Preferably, A– is a halide (such as chloride or bromide), phosphate, sulfate or an anionic pesticide. Propionate, acetate or formate are also suitable as A–. Especially preferably, A– is an anionic pesticide, such as a glyphosate anion or glufosinate anion. If $R^4$ is an oxygen anion, an amine oxide is present. In this case, a further anion such as A– is absent.

In the case of the amine alkoxylate (A), it is preferred that $R^2$ and $R^3$ independently of one another are ethylene, ethylene and propylene, ethylene and butylene, or ethylene, propylene and butylene, and the total of n and m is 2 to 60, preferably 2 to 40, especially preferably 3 to 30 and in particular 5 to 25. In a further preferred embodiment, $R^2$ and $R^3$ are ethylene, ethylene and propylene, ethylene and butylene, or ethylene, propylene and butylene and the total of n and m is 6 to 9, in particular 6.5 to 8.5 and in particular 6.9 to 7.9. In a further preferred embodiment, $R^2$ and $R^3$ are ethylene, ethylene and propylene, ethylene and butylene, or ethylene, propylene and butylene and the total of n and m is 11 to 40, in particular 12 to 30 and in particular 13.5 to 25. In an especially preferred embodiment, $R^1$ and $R^2$ are ethylene, ethylene and propylene, ethylene and butylene, or ethylene, propylene and butylene, and the total of n and m is 6 to 14, in particular 8 to 12 and in particular 9 to 11.

In the case of the amine alkoxylate (A), it is especially preferred that $R^2$ and $R^3$ are ethylene, and the total of n and m is 2 to 60, preferably 2 to 40, especially preferably 3 to 30, and in particular 5 to 25. In a further especially preferred embodiment, $R^2$ and $R^3$ are ethylene and the total of n and m is 6 to 9, in particular 6.5 to 8.5 and in particular 6.9 to 7.9. In a further especially preferred embodiment, $R^2$ and $R^3$ are ethylene and the total of n and m is 11 to 40, in particular 12 to 30 and in particular 13.5 to 25.

Compounds (A) and (AQ) may be present as mixtures of stereoisomers or as isolated stereoisomers. Tautomers and betaines are likewise comprised by the structures (A) and (AQ).

The composition according to the invention will, in most cases, comprise from 0.1 to 90% by weight of the alkoxylate, preferably from 1 to 50% by weight and in particular from 3 to 30% by weight.

The term pesticide refers to at least one active substance selected from the group of the fungicides, insecticides, nematicides, herbicides, safeners, molluscicides, rodenticides and/or growth regulators. Preferred pesticides are fungicides, insecticides, herbicides and growth regulators. Especially preferred pesticides are herbicides and growth regulators. Mixtures of pesticides from two or more of the abovementioned classes may also be used. The skilled worker is familiar with such pesticides, which can be found, for example, in Pesticide Manual, 14th Ed. (2006), The British Crop Protection Council, London. Suitable pesticides are:

A) strobilurins:
azoxystrobin, dimoxystrobin, coumoxystrobin, coumethoxystrobin, enestroburin, fluoxastrobin, kresoxim-methyl, metominostrobin, orysastrobin, picoxystrobin, pyraclostrobin, pyrametostrobin, pyraoxystrobin, pyribencarb, trifloxystrobin, methyl 2-[2-(2,5-dimethylphenyloxymethyl)phenyl]-3-methoxyacrylate, 2-(2-(3-(2,6-dichlorophenyl)-1-methylallylideneaminooxymethyl)phenyl)-2-methoxyimino-N-methylacetamide;

B) carboxamides:
carboxanilides: benalaxyl, benalaxyl-M, benodanil, bixafen, boscalid, carboxin, fenfuram, fenhexamid, flutolanil, furametpyr, isopyrazam, isotianil, kiralaxyl, mepronil, metalaxyl, metalaxyl-M (mefenoxam), ofurace, oxadixyl, oxycarboxin, penflufen (N-(2-(1,3-dimethylbutyl)phenyl)-1,3-dimethyl-5-fluoro-1H-pyrazole-4-carboxamide), penthiopyrad, sedaxane, tecloftalam, thifluzamide, tiadinil, 2-amino-4-methylthiazole-5-carboxanilide, N-(3',4',5'-trifluorobiphenyl-2-yl)-3-difluoromethyl-1-methyl-1H-pyrazole-4-carboxamide, N-(4'-trifluoromethylthiobiphenyl-2-yl)-3-difluoromethyl-1-methyl-1H-pyrazole-4-carboxamide, N-(2-(1,3,3-trimethylbutyl)-phenyl)-1,3-dimethyl-5-fluoro-1H-pyrazole-4-carboxamide;
carboxylic acid morpholides: dimethomorph, flumorph, pyrimorph;
benzamides: flumetover, fluopicolide, fluopyram, zoxamid;
other carboxamides: carpropamid, diclocymet, mandipropamid, oxytetracyclin, silthiofam, N-(6-methoxypyridin-3-yl)cyclopropanecarboxamide;

C) azoles:
triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole;
imidazoles: cyazofamid, imazalil, imazalil sulfate, pefurazoate, prochloraz, triflumizole;
benzimidazoles: benomyl, carbendazim, fuberidazole, thiabendazole;
others: ethaboxam, etridiazole, hymexazole, 2-(4-chlorophenyl)-N-[4-(3,4-dimethoxy-phenyl)isoxazol-5-yl]-2-prop-2-ynyloxyacetamide;

D) nitrogenous heterocyclyl compounds
pyridines: fluazinam, pyrifenox, 3-[5-(4-chlorophenyl)-2,3-dimethylisoxazolidin-3-yl]-pyridine, 3-[5-(4-methylphenyl)-2,3-dimethylisoxazolidin-3-yl]pyridine;
pyrimidines: bupirimate, cyprodinil, diflumetorim, fenarimol, ferimzone, mepanipyrim, nitrapyrin, nuarimol, pyrimethanil;
piperazines: triforine;
pyrroles: fludioxonil, fenpiclonil;
morpholines: aldimorph, dodemorph, dodemorph acetate, fenpropimorph, tridemorph;
piperidines: fenpropidin;
dicarboximides: fluorimid, iprodione, procymidone, vinclozolin;
nonaromatic 5-membered heterocyclic rings: famoxadon, fenamidon, flutianil, octhilinone, probenazole, S-ally 5-amino-2-isopropyl-3-oxo-4-orthotolyl-2,3-dihydropyrazole-1-thiocarboxylate;
others: acibenzolar-S-methyl, amisulbrom, anilazin, blasticidin-S, captafol, captan, quinomethionate, dazomet, debacarb, diclomezine, difenzoquat, difenzoquat methylsulfate, fenoxanil, folpet, oxolinic acid, piperalin, proquinazid, pyroquilon, quinoxyfen, triazoxide, tricyclazole, 2-butoxy-6-iodo-3-propylchromen-4-one, 5-chloro-1-(4,6-dimethoxypyrimidin-2-yl)-2-methyl-1H-benzimidazole, 5-chloro-7-(4-methylpiperidin-1-yl)-6-(2,4,6-trifluorophenyl)-[1,2,4]-triazolo[1,5-a]pyrimidine, 5-ethyl-6-octyl-[1,2,4]triazolo[1,5-a]pyrimidin-7-ylamine;

E) carbamates and dithiocarbamates
thio- and dithiocarbamates: ferbam, mancozeb, maneb, metam, methasulphocarb, metiram, propineb, thiram, zineb, ziram;
carbamates: diethofencarb, benthiavalicarb, iprovalicarb, propamocarb, propamocarb hydrochloride, valiphenal, (4-fluorophenyl) N-(1-(1-(4-cyanophenyl)ethanesulfonyl)-but-2-yl)carbamate;

F) other fungicides
guanidines: dodine, dodine free base, guazatine, guazatine acetate, iminoctadine, iminoctadine triacetate, iminoctadine tris(albesilate);
antibiotics: kasugamycin, kasugamycin hydrochloride hydrate, polyoxins, streptomycin, validamycin A;
nitrophenyl derivatives: binapacryl, dicloran, dinobuton, dinocap, nitrothal-isopropyl, tecnazene;
organometallic compounds: fentin salts such as, for example, fentin acetate, fentin chloride, fentin hydroxide;
sulfurous heterocyclyl compounds: dithianon, isoprothiolane;
organophosphorus compounds: edifenphos, fosetyl, fosetyl-aluminum, iprobenfos, phosphorous acid and its salts, pyrazophos, tolclofos-methyl;
organochlorine compounds: chlorthalonil, dichlofluanid, dichlorphen, flusulfamide, hexachlorobenzene, pencycuron, pentachlorophenol and its salts, phthalide, quintozene, thiophanate-methyl, tolylfluanid, N-(4-chloro-2-nitrophenyl)-N-ethyl-4-methylbenzenesulfonamide;
inorganic active substances: phosphorous acid and its salts, Bordeaux mixture, copper salts such as, for example, copper acetate, copper hydroxide, copper oxychloride, basic copper sulfate, sulfur;
biological products for controlling fungi, plant strengthening products: *Bacillus subtilis* strain NRRL No. B-21661 (for example the products RHAPSODY®, SERENADE®MAX and SERENADE® ASO from AgraQuest, Inc., USA.), *Bacillus pumilus* strain NRRL No. B-30087 (for example SONATA® and BALLAD® Plus from AgraQuest, Inc., USA), *Ulocladium oudemansi* (for example BOTRY-ZEN from BotriZen Ltd., New Zealand), chitosan (for example ARMOUR-ZEN from BotriZen Ltd., New Zealand).
others: biphenyl, bronopol, cyflufenamid, cymoxanil, diphenylamine, metrafenon, mildiomycin, oxine-copper, prohexadione-calcium, spiroxamin, tolylfluanid, N-(cyclo-propylmethoxyimino-(6-difluoromethoxy-2,3-difluorophenyl)methyl)-2-phenyl-acetamide, N'-(4-(4-chloro-3-trifluoromethylphenoxy)-2,5-dimethylphenyl)-N-ethyl-N-methylformamidine, N'-(4-(4-fluoro-3-trifluoromethylphenoxy)-2,5-dimethylphenyl)-N-ethyl-N-methylformamidine, N'-(2-methyl-5-trifluoromethyl-4-(3-trimethylsilanylpropoxy)phenyl)-N-ethyl-N-methylformamidine, N'-

(5-difluoromethyl-2-methyl-4-(3-tri-methylsilanylpropoxy)phenyl)-N-ethyl-N-methylformamidine, N-methyl-(1,2,3,4-tetrahydronaphthalen-1-yl)-2-{1-[2-(5-methyl-3-trifluoromethylpyrazol-1-yl)acetyl]piperidin-4-yl}thiazole-4-carboxylate, N-methyl-(R)-1,2,3,4-tetrahydronaphthalen-1-yl 2-{1-[2-(5-methyl-3-trifluoromethylpyrazol-1-yl)acetyl]piperidin-4-yl}thiazole-4-carboxylate, 6-tert-butyl-8-fluoro-2,3-dimethylquinolin-4-ylacetate, 6-tert-butyl-8-fluoro-2,3-dimethylquinolin-4-yl methoxyacetate, N-methyl-2-{1-[2-(5-methyl-3-trifluoromethyl-1H-pyrazol-1-yl)acetyl]piperidin-4-yl}-N-[(1R)-1,2,3,4-tetrahydronaphthalen-1-yl]-4-thiazolecarboxamide;

G) growth regulators abscisic acid, amidochlor, ancymidole, 6-benzylaminopurine, brassinolide, butralin, chlormequat (chlormequat chloride), choline chloride, cyclanilid, daminozide, dikegulac, dimethipin, 2,6-dimethylpuridine, ethephon, flumetralin, flurprimidol, fluthiacet, forchlorfenuron, gibberellic acid, inabenfid, indole-3-acetic acid, maleic hydrazide, mefluidid, mepiquat (mepiquat chloride), metconazole, naphthaleneacetic acid, N-6-benzyladenine, paclobutrazole, prohexadione (prohexadione-calcium), prohydrojasmone, thidiazuron, triapenthenol, tributylphosphorotrithioate, 2,3,5-triiodo-benzoic acid, trinexapac-ethyl and uniconazole;

H) herbicides acetamide: acetochlor, alachlor, butachlor, dimethachlor, dimethenamid, flufenacet, mefenacet, metolachlor, metazachlor, napropamid, naproanilid, pethoxamid, pretilachlor, propachlor, thenylchlor;

amino acid analogs: bilanafos, glyphosate, glufosinate, sulfosate;

aryloxyphenoxypropionates: clodinafop, cyhalofop-butyl, fenoxaprop, fluazifop, haloxyfop, metamifop, propaquizafop, quizalofop, quizalofop-P-tefuryl;

bipyridyls: diquat, paraquat;

carbamates and thiocarbamates: asulam, butylate, carbetamide, desmedipham, dimepiperat, eptam (EPTC), esprocarb, molinate, orbencarb, phenmedipham, prosulfocarb, pyributicarb, thiobencarb, triallate;

cyclohexanediones: butroxydim, clethodim, cycloxydim, profoxydim, sethoxydim, tepraloxydim, tralkoxydim;

dinitroanilines: benfluralin, ethalfluralin, oryzalin, pendimethalin, prodiamine, trifluralin;

diphenyl ethers: acifluorfen, aclonifen, bifenox, diclofop, ethoxyfen, fomesafen, lactofen, oyfluorfen;

hydroxybenzonitriles: bromoxynil, dichlobenil, ioxynil;

imidazolinones: imazamethabenz, imazamox, imazapic, imazapyr, imazaquin, imazethapyr;

phenoxyacetic acids: clomeprop, 2,4-dichlorophenoxyacetic acid (2,4-D), 2,4-DB, dichlorprop, MCPA, MCPA-thioethyl, MCPB, mecoprop;

pyrazines: chloridazon, flufenpyr-ethyl, fluthiacet, norflurazon, pyridate;

pyridines: aminopyralid, clopyralid, diflufenican, dithiopyr, fluridone, fluroxypyr, picloram, picolinafen, thiazopyr;

sulfonylureas: amidosulfuron, azimsulfuron, bensulfuron, chlorimuron-ethyl, chlorsulfuron, cinosulfuron, cyclosulfamuron, ethoxysulfuron, flazasulfuron, fluceto-sulfuron, flupyrsulfuron, foramsulfuron, halosulfuron, imazosulfuron, iodosulfuron, mesosulfuron, metsulfuron-methyl, nicosulfuron, oxasulfuron, primisulfuron, pro-sulfuron, pyrazosulfuron, rimsulfuron, sulfometuron, sulfosulfuron, thifensulfuron, tria-sulfuron, tribenuron, trifloxysulfuron, triflusulfuron, tritosulfuron, 1-((2-chloro-6-propyl-imidazo[1,2-b]pyridazin-3-yl)sulfonyl)-3-(4,6-dimethoxypyrimidin-2-yl)urea;

triazines: ametryne, atrazine, cyanazine, dimethametryne, ethiozine, hexazinone, metamitron, metribuzine, prometryne, simazine, terbuthylazine, terbutryne, triaziflam;

ureas: chlortoluron, daimuron, diuron, fluometuron, isoproturon, linuron, methabenz-thiazuron, tebuthiuron;

other acetolactate synthase inhibitors: bispyribac-sodium, cloransulam-methyl, diclosulam, florasulam, flucarbazone, flumetsulam, metosulam, orthosulfamuron, penoxsulam, propoxycarbazone, pyribambenz-propyl, pyribenzoxim, pyriftalide, pyriminobac-methyl, pyrimisulfan, pyrithiobac, pyroxasulfon, pyroxsulam;

others: amicarbazone, aminotriazole, anilofos, beflubutamid, benazolin, bencarbazone, benfluresate, benzofenap, bentazone, benzobicyclon, bromacil, bromobutide, butafenacil, butamifos, cafenstrole, carfentrazone, cinidon-ethyl, chlorthal, cinmethylin, clomazone, cumyluron, cyprosulfamid, dicamba, difenzoquat, diflufenzopyr, *Drechslera monoceras*, endothal, ethofumesate, etobenzanid, fentrazamide, flumiclorac-pentyl, flumioxazin, flupoxam, fluorochloridon, flurtamon, indanofan, isoxaben, isoxaflutol, lenacil, propanil, propyzamide, quinclorac, quinmerac, mesotrione, methylarsenic acid, naptalam, oxadiargyl, oxadiazone, oxaziclomefon, pentoxazone, pinoxaden, pyraclonil, pyraflufen-ethyl, pyrasulfotol, pyrazoxyfen, pyrazolynate, quinoclamin, saflufenacil, sulcotrione, sulfentrazone, terbacil, tefuryltrione, tembotrione, thiencarbazone, topramezone, 4-hydroxy-3-[2-(2-methoxyethoxymethyl)-6-trifluoromethylpyridin-3-carbonyl]bicyclo[3.2.1]oct-3-en-2-one, ethyl (3-[2-chloro-4-fluoro-5-(3-methyl-2,6-dioxo-4-trifluoromethyl-3,6-dihydro-2H-pyrimidin-1-yl)phenoxy]pyridin-2-yloxy)acetate, methyl 6-amino-5-chloro-2-cyclo-propylpyrimidine-4-carboxylate, 6-chloro-3-(2-cyclopropyl-6-methylphenoxy)-pyridazin-4-ol, 4-amino-3-chloro-6-(4-chlorophenyl)-5-fluoropyridin-2-carboxylic acid, methyl 4-amino-3-chloro-6-(4-chloro-2-fluoro-3-methoxyphenyl)pyridin-2-carboxylate and methyl 4-amino-3-chloro-6-(4-chloro-3-dimethylamino-2-fluorophenyl)pyridin-2-carboxylate;

I) insecticides organo(thio)phosphates: acephate, azamethiphos, azinphos-methyl, chlorpyrifos, chlorpyrifos-methyl, chlorfenvinphos, diazinon, dichlorvos, dicrotophos, dimethoat, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin, insect growth inhibitors: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazin; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramate;

nicotine receptor agonists/antagonists: clothianidin, dinotefuran, imidacloprid, thiamethoxam, nitenpyram, acetamiprid, thiacloprid, 1-(2-chlorothiazol-5-ylmethyl)-2-nitrimino-3,5-dimethyl-[1,3,5]triazinane;

GABA antagonists: endosulfan, ethiprole, fipronil, vaniliprole, pyrafluprole, pyriprole, N-5-amino-1-(2,6-dichloro-4-methylphenyl)-4-sulfinamoyl-1H-pyrazole-3-thiocarbox-amide;

macrocyclic lactones: abamectin, emamectin, milbemectin, lepimectin, spinosad, spinetoram;

mitochondrial electron transport chain inhibitor (METI) I acaricides: fenazaquin, pyridaben, tebufenpyrad, tolfenpyrad, flufenerim;

METI II and III substances: acequinocyl, fluacyprim, hydramethylnone;

decouplers: chlorfenapyr;

inhibitors of oxidative phosphorylation: cyhexatin, diafenthiuron, fenbutatin oxide, propargite;

insect ecdysis inhibitors: cryomazin;

'mixed function oxidase' inhibitors: piperonyl butoxide;

sodium channel blockers: indoxacarb, metaflumizon;

others: benclothiaz, bifenazate, cartap, flonicamid, pyridalyl, pymetrozin, sulfur, thiocyclam, flubendiamid, chlorantraniliprole, cyazypyr (HGW86); cyenopyrafen, flupyrazofos, cyflumetofen, amidoflumet, imicyafos, bistrifluoron and pyrifluquinazone.

Preferably, pesticides comprise at least one pesticide with at least one H-acidic group (such as carboxylic acid group, phosphonic acid group, phosphinic acid group) or their anionic salts (for example mono-, di- or trisalts). These anionic salts of the pesticides with an H-acidic group are also suitable as anionic pesticides in group A–. Preferred pesticides with an H-acidic group are herbicides with an H-acidic group. Examples of herbicides with an H-acidic group are amino acid analogs (such as glyphosate or glufosinate) or imidazolinones (such as imazamethabenz, imazamox, imazapic, imazapyr, imazaquin, imazethapyr). Especially preferred pesticides with an H-acidic group are glyphosate and glufosinate. In a further preferred embodiment, pesticides with an H-acidic group are imidazolinones.

Especially preferably, the pesticide comprises a pesticide with an H-acidic group and a further pesticide. In a further embodiment, the pesticide comprises mixtures of at least two pesticides with an H-acidic group, and optionally further pesticides (such as at least one fungicide, herbicide, insecticide and/or safener, fungicides and/or herbicides being preferred).

In a further preferred embodiment, the pesticide comprises glyphosate (for example as the free salt, sodium salt, sesquisodium salt, potassium salt, dipotassium salt, ammonium salt, diammonium salt, dimethylammonium salt, trimesium salt or isopropylamine salt) or glufosinate (for example as the ammonium salt). Especially preferably, the pesticide comprises glyphosate (for example as the potassium salt, ammonium salt, isopropylamine salt). Especially preferably, the pesticide comprises glyphosate or glufosinate, and additionally a further herbicide. In a further preferred embodiment, the pesticide comprises glyphosate or glufosinate, and additionally a further pesticide (such as at least one fungicide, herbicide, insecticide and/or safener, fungicides and/or herbicides being preferred).

The compositions according to the invention can furthermore also comprise adjuvants conventionally used for agrochemical formulations, the choice of the adjuvants depending on the specific use form, the type of formulation or the active substance. Examples of suitable adjuvants are solvents, solid carriers, surface-active substances (such as surfactants, solubilizers, protective colloids, wetters and tackifiers), organic and inorganic thickeners, bactericides, antifreeze agents, antifoams, optionally colorants and adhesives (for example for the treatment of seed) or conventional adjuvants for bait formulation (for example attractants, feedants, bittering substances).

Suitable solvents are water or organic solvents such as mineral oil fractions of medium to high boiling point such as kerosene and diesel oil, furthermore coal tar oils and oils of vegetable or animal origin, aliphatic, cyclic and aromatic hydrocarbons, for example paraffins, tetrahydronaphthalene, alkylated naphthalenes and their derivatives, alkylated benzenes and their derivatives, alcohols such as methanol, ethanol, propanol, butanol and cyclohexanol, glycols, ketones such as cyclohexanone, gamma-butyrolactone, dimethyl fatty acid amides, fatty acids and fatty acid esters, and strongly polar solvents, for example amines such as N-methylpyrrolidone. In principle, it is also possible to use solvent mixtures and mixtures of the abovementioned solvents and water.

Solid carriers are mineral earths such as silicas, silica gels, silicates, talc, kaolin, limestone, lime, chalk, bole, loess, clay, dolomite, diatomaceous earth, calcium and magnesium sulfate, magnesium oxide, ground synthetic materials, fertilizers such as ammonium sulfate, ammonium phosphate, ammonium nitrate, ureas and vegetable products such as cereal meal, tree bark meal, wood meal and nutshell meal, cellulose powders or other solid carriers.

Surface-active substances (adjuvants, wetters, tackifiers, dispersants or emulsifiers) which are suitable are the alkali metal, alkaline-earth metal, ammonium salts of aromatic sulfonic acids, for example of lignosulfonic acid (Borresperse® types, Borregaard, Norway), phenolsulfonic acid, naphthalenesulfonic acid (Morwet® types, Akzo Nobel, USA) and dibutylnaphthalenesulfonic acid (Nekal® types, BASF, Germany), and of fatty acids, alkyl- and alkylarylsulfonates, alkyl ether, lauryl ether and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonyiphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene or polyoxypropylene alkyl ethers, lauryl alcohol polyglycol ether acetate, sorbitol esters, lignin-sulfite liquors and proteins, denatured proteins, polysaccharides (for example methylcellulose), hydrophobe-modified starches, polyvinyl alcohol (Mowiol® types, Clariant, Switzerland), polycarboxylates (Sokalan® types, BASF, Germany), polyalkoxylates, polyvinylamine (Lupamin® types, BASF, Germany), polyethyleneimine (Lupasol® types, BASF, Germany), polyvinylpyrrolidone and their copolymers.

The composition according to the invention may comprise from 0.1 to 40% by weight, preferably from 1 to 30 and in particular from 2 to 20% by weight of surface-active substances, the amount of the alkoxylate (A) and (AQ) not being taken into consideration.

Suitable thickeners are compounds which impart to the formulation a modified flow behavior, i.e. high viscosity at rest and low viscosity in the agitated state. Examples are polysaccharides, proteins (such as casein or gelatins), synthetic polymers, or inorganic layered minerals. Such thickeners are commercially available, for example Xanthan Gum (Kelzan®, CP Kelco, USA), Rhodopol® 23 (Rhodia, France) or Veegum® (R. T. Vanderbilt, USA) or Attaclay® (Engelhard Corp., NJ, USA). The thickener content in the formulation depends on the efficacy of the thickener. The skilled worker will choose such a content that the desired viscosity of the formulation is obtained. The content will amount to from 0.01 to 10% by weight in most cases.

Bactericides may be added in order to stabilize the composition. Examples of bactericides are those based on dichlorophene and benzyl alcohol hemiformal and also isothiazolinone derivatives such as alkylisothiazolinones and benzoisothiazolinones (Acticide® MBS from Thor Chemie). Examples of suitable antifreeze agents are ethylene glycol, propylene glycol, urea and glycerol. Examples of antifoams are silicone emulsions (such as, for example, Silikon® SRE, Wacker, Germany or Rhodorsil®, Rhodia, France), long-chain alcohols, fatty acids, salts of fatty acids, organofluorine compounds and mixtures of these.

The composition according to the invention can preferably be present in the form of an agrochemical formulation. Examples of such formulations and their preparation are:
i) Water-soluble concentrates (SL, LS): 10 parts by weight of the active substances are dissolved using 90 parts by weight of water or a water-soluble solvent. Alternatively, wetters or other adjuvants are added. Upon dilution in water, the active substance dissolves. This gives a composition with an active substance content of 10% by weight.
ii) Dispersible concentrates (DC): 20 parts by weight of the active substances are dissolved in 70 parts by weight of cyclohexanone with addition of 10 parts by weight of a dispersant, for example polyvinylpyrrolidone. Upon dilution in water, a dispersion is obtained. The active substance content amounts to 20% by weight
iii) Emulsifiable concentrates (EC): 15 parts by weight of the active substances are dissolved in 75 parts by weight of xylene with addition of calcium dodecylbenzene-sulfonate and castor oil ethoxylate (in each case 5 parts by weight). Upon dilution in water, an emulsion is obtained. The composition has an active substance content of 15% by weight.
iv) Emulsions (EW, EO, ES): 25 parts by weight of the active substances are dissolved in 35 parts by weight of xylene with addition of calcium dodecylbenzene-sulfonate and castor oil ethoxylate (in each case 5 parts by weight). Using an emulsifier (for example Ultra-Turrax), this mixture is placed into 30 parts by weight of water and made into a homogeneous emulsion. Upon dilution in water, an emulsion results. The composition has an active substance content of 25% by weight.
v) Suspensions (SC, OD, FS): 20 parts by weight of the active substances are comminuted with addition of 10 parts by weight of dispersants and wetters and 70 parts by weight of water or an organic solvent in a stirred-ball mill to give a finely divided active substance suspension. Upon dilution in water, a stable suspension of the active substance is obtained. The active substance content in the composition amounts to 20% by weight.
vi) Water-dispersible and water-soluble granules (WG, SG): 50 parts by weight of the active substances are ground finely with addition of 50 parts by weight of dispersants and wetters and prepared as water-dispersible or water-soluble granules by means of technical apparatuses (for example extrusion, spray tower, fluidized bed). Upon dilution in water, a stable dispersion or solution of the active substance is obtained. The composition has an active substance content of 50% by weight.
vii) Water-dispersible and water-soluble powders (WP, SP, SS, WS): 75 parts by weight of the active substances are ground in a rotor-stator mill with addition of 25 parts by weight of dispersants and wetters and also silica gel. Upon dilution in water, a stable dispersion or solution of the active substance is obtained. The active substance content of the composition amounts to 75% by weight.
viii) Gels (GF): in a ball mill, 20 parts by weight of the active substances, 10 parts by weight of dispersant, 1 part by weight of gelling agent and 70 parts by weight of water or an organic solvent are ground to give a fine suspension. Upon dilution with water, a stable suspension with an active substance content of 20% by weight is obtained.
ix) Dusts (DP, DS): 5 parts by weight of the active substances are ground finely and mixed intimately with 95 parts by weight of finely divided kaolin. This gives a dust with an active substance content of 5% by weight.
x) Granules (GR, FG, GG, MG): 0.5 part by weight of the active substances is ground finely and associated with 99.5 parts by weight of carriers. Conventional methods to this end are extrusion, spray-drying or the fluidized bed. This gives granules for direct application with an active substance content of 0.5% by weight.
xi) ULV solutions (UL): 10 parts by weight of the active substances are dissolved in 90 parts by weight of an organic solvent, for example xylene. This gives a composition to be applied directly with an active substance content of 10% by weight.

In general, the compositions comprise from 0.01 to 95% by weight, preferably from 0.1 to 90% by weight, of the pesticides.

The user will generally use the composition according to the invention for use in a premetering device, in a knapsack sprayer, in a spray tank or in a spraying aircraft.

Here, the formulation is brought to the desired use concentration with water and/or buffer, optionally with addition of further auxiliaries, whereby the ready-to-use spray mixture (known as a tank mix) is obtained. Usually, 50 to 500 liters of the ready-to-use spray mixture are applied per hectare of utilizable agricultural area, preferably from 100 to 400 liters. In specific segments, these amounts can also be exceeded (for example pomiculture) or undercut (for example aircraft application). The active substance concentrations in the ready-to-use preparations may be varied within substantial ranges. In general, they are between 0.0001 and 10%, preferably between 0.01 and 1%.

Oils of various types, wetters, drift-reducing agents, stickers, spreaders, adjuvants, fertilizers, plant-strengthening products, trace elements, herbicides, bactericides, fungicides and/or pesticides may be added to the active substances or to the preparations comprising them, optionally also to the tank mix, immediately prior to use. These products can be admixed to the compositions according to the invention in the weight ratio 1:100 to 100:1, preferably 1:10 to 10:1. Adjuvants which are suitable within this context are in particular: organic-modified polysiloxanes, for example Break Thru S 240®; alcohol alkoxylates, for example Atplus® 245, Atplus® MBA 1303, Plurafac® LF 300 and Lutensol® ON 30; EO/PO block polymers, for example Pluronic® RPE 2035 and Genapol® B; alcohol ethoxylates, for example Lutensol® XP 80; and sodium dioctyl sulfosuccinate, for example Leophen® RA.

Depending on the nature of the desired effect, the application rates of the active substance when used in plant protection are between 0.001 and 2.0 kg of active substance per ha, preferably between 0.005 and 2 kg per ha, especially preferably between 0.05 and 0.9 kg per ha, in particular between 0.1 and 0.75 kg per ha.

The present invention furthermore relates to a method of controlling phytopathogenic fungi and/or undesired vegetation and/or undesired insect or mite attack and/or for regulating the growth of plants, wherein the composition according to the invention is allowed to act on the respective pests, their environment or the plants to be protected from the respective pest, on the soil and/or on undesirable plants and/or the crop plants and/or their environment.

Examples of suitable crop plants are cereals, for example wheat, rye, barley, triticale, oats or rice; beet, for example sugar or fodder beet; pome fruit, stone fruit and soft fruit, for example apples, pears, plums, peaches, almonds, cherries, strawberries, raspberries, currants or gooseberries; legumes, for example beans, lentils, peas, lucerne or soybeans; oil crops, for example oilseed rape, mustard, olives, sunflowers, coconut, cacao, castor beans, oil palm, peanuts or soybeans; cucurbits, for example pumpkins/squash, cucumbers or melons; fiber crops, for example cotton, flax, hemp or jute; citrus fruit, for example oranges, lemons, grapefruit or tangerines; vegetable plants, for example spinach, lettuce, asparagus, cabbages, carrots, onions, tomatoes, potatoes, pumpkin/squash or capsicums; plants of the laurel family, for example avocados, cinnamon or camphor; energy crops and industrial feedstock crops, for example maize, soybeans, wheat, oilseed rape, sugar cane or oil palm; maize; tobacco; nuts; coffee; tea; bananas; wine (dessert grapes and grapes for vinification); hops; grass, for example turf; sweetleaf (*Stevie rebaudania*); rubber plants; ornamentals and forest plants, for example flowers, shrubs, deciduous trees and coniferous trees, and propagation material, for example seeds, and harvested produce of these plants.

The term crop plants also includes those plants which have been modified by breeding, mutagenesis or recombinant methods, including the biotechnological agricultural products which are on the market or in the process of being developed. Genetically modified plants are plants whose genetic material has been modified in a manner which does not occur under natural conditions by hybridizing, mutations or natural recombination (i.e. recombination of the genetic material). Here, one or more genes will, as a rule, be integrated into the genetic material of the plant in order to improve the plant's properties. Such recombinant modifications also comprise posttranslational modifications of proteins, oligo- or polypeptides, for example by means of glycosylation or binding polymers such as, for example, prenylated, acetylated or farnesylated residues or PEG residues.

Examples which may be mentioned are plants which, as the result of plant-breeding and recombinant measures, have acquired a tolerance for certain classes of herbicides, such as hydroxyphenylpyruvate dioxygenase (HPPD) inhibitors, acetolactate synthase (ALS) inhibitors such as, for example, sulfonylureas (EP-A 257 993, U.S. Pat. No. 5,013,659) or imidazolinones (for example U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073), enolpyruvylshikimate 3-phosphate synthase (EPSPS) inhibitors such as, for example, glyphosate (see, for example, WO 92/00377), glutamine synthetase (GS) inhibitors such as, for example, glufosinate (see, for example, EP-A 242 236, EP-A 242 246) or oxynil herbicides (see, for example, U.S. Pat. No. 5,559,024). For example, breeding and mutagenesis have given rise to Clearfield® oilseed rape (BASF SE, Germany), which features tolerance for imidazolinones, for example imazamox. With the aid of recombinant methods, crop plants such as soybeans, cotton, maize, beet and oilseed rape have been generated which are resistant to glyphosate or glufosinate, and these are available by the brand names RoundupReady® (glyphosate-resistant, Monsanto, U.S.A.) and Liberty Link® (glufosinate-resistant, Bayer CropScience, Germany).

Also comprised are plants which, with the aid of recombinant measures, produce one or more toxins, for example those from the bacterial strain *Bacillus*. Toxins which are produced by such genetically modified plants comprise, for example, insecticidal proteins of *Bacillus* spp., in particular from *B. thuringiensis*, such as the endotoxins Cry1Ab, Cry1Ac, Cry1F, Cry1Fa2, Cry2Ab, Cry3A, Cry3Bb1, Cry9c, Cry34Ab1 or Cry35Ab1; or vegetative insecticidal proteins (VIPs), for example VIP1, VIP2, VIP3, or VIP3A; insecticidal proteins from nematode-colonizing bacteria, for example *Photorhabdus* spp. or *Xenorhabdus* spp.; toxins from animal organisms, for example wasp, spider or scorpion toxins; fungal toxins, for example from Streptomycetes; plant lectins, for example from pea or barley; agglutinins; proteinase inhibitors, for example trypsin inhibitors, serine protease inhibitors, patatin, cystatin or papain inhibitors; ribosome-inactivating proteins (RIPs), for example ricin, maize RIP, abrin, luffin, saporin or bryodin; steroid-metabolizing enzymes, for example 3-hydroxysteroid oxidase, ecdysteroid IDP glycosyl transferase, cholesterol oxidase, ecdysone inhibitors or HMG CoA-reductase; ion channel blockers, for example inhibitors of sodium or calcium channels; juvenile hormone esterase; receptors for the diuretic hormone (helicokinin receptors); stilbene synthase, bibenzyl synthase, chitinases and glucanases. These toxins can also be produced, in the plants, in the form of pretoxins, hybrid proteins, truncated or otherwise modified proteins. Hybrid proteins are distinguished by a novel combination of different protein domains (see, for example, WO 2002/015701). Further examples of such toxins or genetically modified plants which produce these toxins are disclosed in EP-A 374 753, WO 93/07278, WO 95/34656, EP-A 427 529, EP-A 451 878, WO 03/18810 and WO 03/52073. The methods for generating these genetically modified plants are known to the skilled worker and explained, for example, in the abovementioned publications. A large number of the abovementioned toxins impart to the plants which produce them a tolerance for pests from all taxonomic classes of the arthropods, in particular beetles (Coeleropta), dipterans (Diptera) and lepidopterans (Lepidoptera) and nematodes (Nematoda). Genetically modified plants which produce one or more genes which code for insecticidal toxins are described for example in the abovementioned publications and are in some cases commercially available such as, for example, YieldGard® (maize varieties which produce the toxin Cry1Ab), YieldGard® Plus (maize varieties which produce the toxins Cry1Ab and Cry3Bb1), Starlink® (maize varieties which produce the toxin Cry9c), Herculex® RW (maize varieties which produce the toxins Cry34Ab1, Cry35Ab1 and the enzyme phosphinothricin N-acetyltransferase [PAT]); NuCOTN® 33B (cotton varieties which produce the toxin Cry1Ac), Bollgard® I (cotton varieties which produce the toxin Cry1Ac), Bollgard® II (cotton varieties which produce the toxins Cry1Ac and Cry2Ab2); VIPCOT® (cotton varieties which produce a VIP toxin); NewLeaf® (potato varieties which produce the toxin Cry3A); Bt-Xtra®, NatureGard®, KnockOut®, BiteGard®, Protecta®, Bt11 (for example Agrisure® CB) and Bt176 from Syngenta Seeds SAS, France, (maize varieties which produce the toxin Cry1Ab and the PAT enzyme), MIR604 from Syngenta Seeds SAS, France (maize varieties which produce a modified version of the toxin Cry3A, see in this context WO 03/018810), MON 863 from Monsanto Europe S.A., Belgium (maize varieties which produce the toxin Cry3Bb1), IPC 531 from Monsanto Europe S.A., Belgium (cotton varieties which produce a modified version of the toxin Cry1Ac) and 1507 from Pioneer Overseas Corporation, Belgium (maize varieties which produce the toxin Cry1F and the PAT enzyme).

Also comprised are plants which, with the aid of recombinant measures, produce one or more proteins which bring about an increased resistance to, or ability to withstand, bacterial, viral or fungal pathogens such as, for example, so-called pathogenesis-related proteins (PR proteins, see EP-A 0 392 225), resistance proteins (for example potato varieties which produce two resistance genes against *Phytophthora infestans* from the Mexican wild potato *Solanum bulbocastanum*) or T4 lysozyme (for example potato varieties which, as the result of the production of this protein, are resistant to bacteria such as *Erwinia amylvora*).

Also comprised are plants whose productivity has been improved with the aid of recombinant methods, for example by increasing the yield potential (for example biomass, grain yield, starch content, oil content or protein content), the tolerance for drought, salt or other limiting environmental factors, or the resistance to pests and fungal, bacterial and viral pathogens.

Also comprised are plants whose constituents, in particular for improving human or animal nutrition, have been modified with the aid of recombinant methods, for example by oil plants producing health-promoting long-chain omega-3-fatty acids or monounsaturated omega-9-fatty acids (for example Nexera® oilseed rape, DOW Agro Sciences, Canada).

The present invention also relates to seed (such as seeds or other plant propagation materials) comprising the composition according to the invention. Plant propagation materials can be treated preventively with the composition according to the invention at the point of or even before sowing or at the point of or even before transplanting. For the treatment of seed, one will generally use water-soluble concentrates (LS), suspensions (FS), dusts (DS), water-dispersible and water-soluble powders (WS, SS), emulsions (ES), emulsifiable concentrates (EC) and gels (GF). These compositions can be applied to the propagation materials, in particular seed, in undiluted form or, preferably, in diluted form. Here, the composition in question can be diluted 2- to 10-fold, so that from 0.01 to 60% by weight, preferably from 0.1 to 40% by weight, of active substance is present in the compositions used for the seed dressing. The application may be effected before or during sowing. The treatment of plant propagation material, in particular the treatment of seed, is known to the skilled worker and carried out by dusting, coating, pelleting, dipping or soaking the plant propagation material, the treatment preferably being carried out by pelleting, coating and dusting or by in-furrow treatment so that, for example, untimely early germination of the seed is prevented. It is preferred to use suspensions for the treatment of seed. Usually, such compositions comprise from 1 to 800 g/l of active substance, from 1 to 200 g/l of surfactants, from 0 to 200 g/l of antifreeze agents, from 0 to 400 g/l of binders, from 0 to 200 g/l of colorants and solvent, preferably water.

The present invention furthermore relates to an alkoxylate, wherein the alkoxylate is an amine alkoxylate (A)

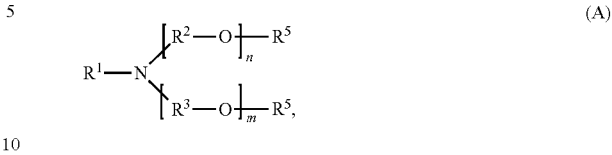

(A)

where $R^1$ is a branched aliphatic alkyl radical $C_9H_{19}$, $R^2$, $R^3$, and $R^7$ independently of one another are ethylene, propylene, butylene or a mixture of these, $R^4$ is an H, —OH, —$OR^6$, —$[R^7$—$O]_p$—$R^5$, $C_1$-$C_6$-alkyl or an oxygen anion, $R^5$ is an H, $C_1$-$C_6$-alkyl, $C_2$-$C_6$-alkenyl, $C_2$-$C_6$-alkynyl, —$SO_3R^a$, —$P(O)OR^bOR^c$, —$CH_2CO_2R^d$ or —$C(O)R^e$, $R^6$ is a $C_1$-$C_6$-alkyl, $C_2$-$C_6$-alkenyl or $C_2$-$C_6$-alkinyl, $R^a$ and $R^d$ independently of one another are an H, inorganic or organic cations, $R^b$ and $R^c$ independently of one another are an H, inorganic or organic cations, $C_1$-$C_6$-alkyl, $C_2$-$C_6$-alkenyl or $C_2$-$C_6$-alkynyl, $R^e$ is $C_1$-$C_{22}$-alkyl, $C_6$-$C_{22}$-aryl, $C_7$-$C_{22}$-alkylaryl, n, m and p independently of one another are a value from 1 to 30, and A– is an agriculturally acceptable anion, or, if $R^3$ is an oxygen anion, A– is absent.

Further preferred embodiments are as described above.

The present invention furthermore relates to an alkoxylate, wherein the alkoxylate is a quaternized derivative (AQ)

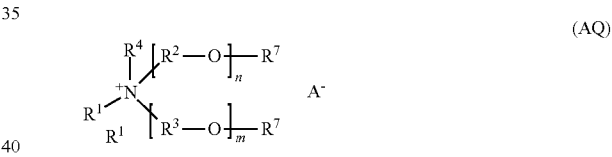

(AQ)

of the amine alkoxylate (A), where $R^1$ is a branched aliphatic alkyl radical $C_9H_{19}$, $R^2$, $R^3$, and $R^7$ independently of one another are ethylene, propylene, butylene or a mixture of these, $R^4$ is an H, —OH, —$OR^6$, —$[R^7$—$O]_p$—$R^5$, $C_1$-$C_6$-alkyl or an oxygen anion, $R^5$ is an H, $C_1$-$C_6$-alkyl, $C_2$-$C_6$-alkenyl, $C_2$-$C_6$-alkynyl, —$SO_3R^a$, —$P(O)OR^bOR^b$, $CH_2CO_2R^d$ or —$C(O)R^e$, $R^6$ is a $C_1$-$C_6$-alkyl, $C_2$-$C_6$-alkenyl or $C_2$-$C_6$-alkinyl, $R^a$ and $R^d$ independently of one another are an H, inorganic or organic cations, $R^b$ and $R^c$ independently of one another are an H, inorganic or organic cations, $C_1$-$C_6$-alkyl, $C_2$-$C_6$-alkenyl or $C_2$-$C_6$-alkynyl, $R^e$ is $C_1$-$C_{22}$-alkyl, $C_6$-$C_{22}$-aryl, $C_7$-$C_{22}$-alkylaryl, n, m and p independently of one another are a value from 1 to 30, and A– is an agriculturally acceptable anion, or, if $R^3$ is an oxygen anion, A– is absent.

Here, A– is preferably a halide (such as chloride or bromide), phosphate, sulfate or an inorganic pesticide. A– is especially preferably an inorganic pesticide, such as glyphosate anion or glufosinate anion. Further preferred embodiments are as described above.

The present invention furthermore relates to processes for the preparation of the amine alkoxylate (A) or a quaternized derivative (AQ) of the amine alkoxylate (A), comprising the alkoxylation of amines $R^1$—$NH_2$ with ethylene oxide, propylene oxide, butylene oxide or a mixture of these.

The present invention furthermore relates to the amine $R^1$—$NH_2$. It is an important intermediate for the preparation of the amine alkoxylate (A) or of a quaternized derivative (AQ) of the amine alkoxylate (A). Preferred embodiments of $R^1$ are as described above. The amines $R^1$—$NH_2$ can be prepared by reacting ammonia with alcohols $R^1$—OH. Suitable catalysts and reaction conditions are described in U.S. Pat. No. 5,808,158.

The alcohols $R^1$—OH are generally known (for example CAS No. 27458-94-2) and commercially available, for example as Isononanol INA from Evonik Oxeno GmbH, Isononanol from OXEA Corporation, or Nonanol N from BASF SE. The isononanol content is usually at least 70% by weight, preferably at least 95% by weight and in particular at least 99% by weight.

In principle, the alcohols $R^1$—OH can be synthesized by any method as long as they have in each case the degree of branching described.

$R^1$—OH can preferably be prepared starting from a hydrocarbon mixture comprising butenes, for example as described in WO 2000/63151:
a) In a first step, butenes are dimerized to give a mixture of isomeric octenes.
b) The octene mixture of a) is subsequently hydroformylated to give C9-aldehydes.
c) The aldehyde of b) is to give isononanols.

The details of the synthesis are generally known to the skilled worker, see, for example, WO 2000/63151 [step a) see page 6, line 2 to page 8, line 7; step b) see page 8, line 9 to page 9, line 30; step c) see page 9, line 32 to page 10, line 16). A particularly suitable alcohol $R^1$—OH can be prepared as described in WO 2000/63151 Example 1, process step 1 and 2 (page 13, line 35 to page 14, line 33).

The alkoxylation can be catalyzed by strong bases, such as alkali metal hydroxides and alkaline earth metal hydroxides, Brönsted acids or Lewis acids, such as $AlCl_3$, $BF_3$. Catalysts such as hydrotalcite or DMC may be used for alcohol alkoxylates with a narrow distribution. The alkoxylation is preferably carried out at temperatures in the range of approximately 80 to 250° C., preferably approximately 100 to 220° C. The pressure is preferably between ambient pressure and 600 bar. If desired, the alkylene oxide may comprise an admixture of inert gas, for example of approximately 5 to 60%.

The quaternized derivative (AQ) of the amine alkoxylate (A) can be prepared in a further reaction step by quaternizing the amine alkoxylate (A). To introduce the radical $R^4$ into the amine alkoxylate (A), the latter may be reacted for example with an alkylation reagent such as methyl chloride, dimethyl sulfate or butyl chloride. To introduce the one oxygen anion into the amine alkoxylate (A), the latter may be oxidized, for example by reacting the amino group with hydrogen peroxide, peracids (such as meta-chloroperbenzoic acid or peracetic acid) or peroxomonosulfuric acid.

The quaternized derivatives (AQ) where $R^4$=H can be prepared by simple protonation of starting compounds of the structure (A). The quaternized derivatives (AQ) where $R^4$=OH can be prepared by simple protonation of starting compounds (AQ) where $R^4$=oxygen anion. Acids which are suitable for the protonation are organic acids (for example $C_1$- to $C_{20}$-carboxylic acids, in particular benzoic acid) or inorganic acids (for example hydrochloric acid, phosphoric acid or sulfuric acid). Others which are likewise suitable are H-acidic pesticides such as, for example, glyphosate-acid or glyphosate-monosalts. The protonation can be carried out in a separate synthesis, so that the quaternized derivative (AQ) can be isolated. It is also possible to carry out the protonation by mixing the starting compounds with one or more acids in the composition or in the spray mixture.

The present invention also relates to the use of the amine alkoxylate (A) or of a quaternized derivative (AQ) of the amine alkoxylate (A) as described above as auxiliary in pesticide-comprising spray mixtures. The auxiliary is preferably an activity-enhancing auxiliary. Such activity-enhancing auxiliaries are also referred to as adjuvants. They enhance or accelerate the activity of pesticides in comparison with the activity of the pesticide in the absence of the adjuvant.

The advantages of the invention are high stability of the formulation and of the spray mixture, little wind-caused drift in the case of spray applications, good adhesion of the formulation on the surface of the treated plants, increased solubility of the pesticides in the formulation, increased permeation of the pesticides into the plant and, as a result, more rapid and enhanced activity. An important advantage is the low toxicity of the novel alkoxylates, in particular the low aquatic toxicity. A further advantage is the simple handling of these alkoxides since gel formation does not occur for example when incorporating them into formulations. Another advantage is the low toxicity to crop plants, i.e. low phytotoxic effects. A further advantage is that branched nonanols are available on an industrial scale (annual production worldwide several hundred thousand (!) tonnes), since they are also precursors of plasticizers and can be prepared from inexpensive C4 raw materials.

The examples which follow illustrate the invention without imposing any limitation.

EXAMPLES

Example 1

Preparation of Branched $C_9$-amine from $C_9$-alcohol

The $C_9$-alcohol employed was Nonanol N, which is commercially available from BASF SE (a mixture of saturated, isomeric primary nonyl alcohols, CAS 248-471-3, boiling range 195-203° C. (DIN 51751), refractive index 1.4353, dynamic viscosity 12.95 mPas at 20° C. (DIN 51562), specific gravity 0.8335 g/ml (DIN 53217)).

The $C_9$-alcohol (1450 g) and an alcohol amination catalyst (described in EP 696 572 A1; 4.8% by weight based on $C_{17}$-alcohol) were introduced in the autoclave and the autoclave was flushed with nitrogen and hydrogen. Then, 2500 g of ammonia were charged and warmed with stirring. After a reaction time of ten hours at 235° C. and an $H_2$ pressure of 280 bar, the $C_9$-amine obtained was filtered and freed from water on a rotary evaporator (water content less than 0.1% by weight).

Example 2

Alkoxylation of Branched $C_9$-amine with 5, 7 or 10 EO Units

First, 715 g (5 mol) of $C_9$-amine of example 1 were treated with 23.1 g of water. The mixture was flushed with nitrogen and then 440 g (10 mol) of ethylene oxide (EO) were metered in at 100° C. over 12 h, the metering being weight-controlled. Thereafter, stirring was continued for 6 h at 100° C. The mixture was subsequently dehydrated for 2 hours in vacuo at 90° C. This gave a yield of 1164 g (=101% of theory) with an amine number of 239 mg of KOH/g (243 mg of KOH/g in theory). In the second step, 2.3 g of 50% strength KOH were added to 300 g (1.3 mol) of this precursor, and the mixture was dehydrated for 2 hours in vacuo at 90° C. After flushing with nitrogen, 286 g (6.5 mol) of ethylene oxide were metered in at 120° C. over 6 h, the metering being weight-controlled. Thereafter, stirring was continued for 6 h at 120° C. The product was degassed in vacuo and neutralized with a few drops of acetic acid. This gave a yield of 592 g (101% of theory) of a colorless liquid of low viscosity (hereinbelow "iso-$C_9$-7 EO"; amine number 119 mg of KOH/g (124 mg of KOH/g in theory).

Starting from the amine of example 1, iso-$C_9$-5 EO (i.e. ethoxylated with a total of 5 EO groups) and iso-$C_9$-10 EO (i.e. ethoxylated with a total of 10 EO groups) were also prepared analogously to the preparation of iso-$C_9$-7 EO.

Example 3

Glyphosate SL on Model Plants, Winter Wheat or Soybean

To carry out the greenhouse tests, winter wheat or soybean were sown or potted in loamy sand at a sowing depth of 1-2 cm. As soon as the plants had reached a height of 10 to 25 cm (i.e. approximately 10 to 21 days after sowing), the spray mixtures were applied to the plants in the spray cabinet.

A concentrated formulation comprising glyphosate isopropylammonium dissolved in water and amine alkoxylate of example 2 was diluted with demineralized water and were applied at a water application weight of 375 l/ha (140 g or 280 g of glyphosate/ha and in each case 300 g of amine alkoxylate/ha). Genamine® T-150 ("C16118-amine-15 EO", commercially available from Clariant, Germany), which is an aliphatic C16/18-amine alkoxylated with 15 ethylene oxide, was employed as a comparison. The temperatures during this experimental period, which was 3 to 4 weeks, were between 18-35° C. During this time, the test plants received optimal irrigation, the nutrient supply being provided via the irrigation water.

The herbicidal activity was assessed by scoring the treated plants in comparison with the untreated control plants (Table 1-3). The assessment scale was from 0% to 100% activity. 100% activity means complete dying at least of the aerial plant parts. In contrast, 0% activity means that no differences were observed between treated and untreated plants. The results in Table 1 and 2 confirm the increased activity of the active substance as the result of the addition of the amine alkoxylate.

TABLE 1

| Winter wheat cv. Cubus | | | | |
|---|---|---|---|---|
| Amine alkoxylate | Glyphosate [g/ha] | Activity [%] after 14 days | Activity [%] after 21 days | Activity [%] after 28 days |
| —[a] | 280 | 71 | 81 | 81 |
| —[a] | 140 | 64 | 73 | 73 |
| $C_{16/18}$-15 EO[a] | 280 | 86 | 100 | 100 |
| $C_{16/18}$-15 EO[a] | 140 | 68 | 78 | 78 |
| iso-$C_9$-5 EO | 280 | 90 | 100 | 100 |
| iso-$C_9$-5 EO | 140 | 80 | 98 | 98 |
| iso-$C_9$-7 EO | 280 | 84 | 99 | 100 |
| iso-$C_9$-7 EO | 140 | 75 | 92 | 90 |

TABLE 1-continued

| Winter wheat cv. Cubus | | | | |
|---|---|---|---|---|
| Amine alkoxylate | Glyphosate [g/ha] | Activity [%] after 14 days | Activity [%] after 21 days | Activity [%] after 28 days |
| iso-$C_9$-10 EO | 280 | 88 | 100 | 100 |
| iso-$C_9$-10 EO | 140 | 80 | 94 | 94 |

[a]Comparative experiment, not in accordance with the invention.

TABLE 2

| Soybean cv. Oxford | | | | |
|---|---|---|---|---|
| Amine alkoxylate | Glyphosate [g/ha] | Activity [%] after 14 days | Activity [%] after 21 days | Activity [%] after 28 days |
| —[a] | 140 | 29 | 38 | 38 |
| $C_{16/18}$-15 EO[a] | 140 | 44 | 50 | 50 |
| iso-$C_9$-5 EO | 140 | 54 | 71 | 71 |
| iso-$C_9$-7 EO | 140 | 44 | 54 | 54 |
| iso-$C_9$-10 EO | 140 | 43 | 55 | 56 |

[a]Comparative experiment, not in accordance with the invention.

The invention claimed is:

1. A composition comprising a pesticide selected from the group consisting of glyphosate, glufosinate, and anionic salt thereof, and an alkoxylate, wherein the alkoxylate is an amine alkoxylate (A)

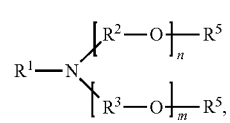

(A)

wherein
R$^1$ is a branched aliphatic alkyl radical $C_9H_{19}$,
R$^2$ and R$^3$ independently of one another are ethylene, propylene, or combinations thereof,
R$^5$ is an H,
n and m independently of one another are a value from 1 to 15, and the total n and m is from 5 to 25.

2. The composition of claim 1, wherein R$^2$ and R$^3$ independently of one another are ethylene or ethylene and propylene.

3. The composition of claim 1, wherein the mean degree of branching of R$^1$ is from 1.01 to 2.5.

4. The composition of claim 1, additionally comprising a further herbicide.

5. A method of controlling undesired vegetation and/or for regulating the growth of plants, comprising applying the composition of claim 1 on the soil, undesirable plants, crop plants and/or their environment.

6. The method of claim 5, wherein R$^2$ and R$^3$ independently of one another are ethylene or ethylene and propylene.

7. The method of claim 5, wherein the mean degree of branching of R$^1$ is from 1.01 to 2.5.

8. The method of claim 5, wherein the composition additionally comprises a further herbicide.

9. A seed treated with the composition of claim 1.

10. The seed of claim 9, wherein R$^2$ and R$^3$ of the alkoxylate are independently of one another ethylene or ethylene and propylene.

* * * * *